United States Patent [19]

Bowen

[11] 4,362,889

[45] Dec. 7, 1982

[54] USE OF A POLYFUNCTIONAL SURFACE-ACTIVE COMONOMER AND OTHER AGENTS TO IMPROVE ADHESION BETWEEN A RESIN OR COMPOSITE MATERIAL AND A SUBSTRATE

[75] Inventor: Rafael L. Bowen, Gaithersburg, Md.

[73] Assignee: The American Dental Association Health Foundation, Washington, D.C.

[21] Appl. No.: 200,989

[22] Filed: Oct. 27, 1980

Related U.S. Application Data

[62] Division of Ser. No. 10,803, Feb. 9, 1979, Pat. No. 4,251,565.

[51] Int. Cl.$^3$ .......................................... C07C 69/587
[52] U.S. Cl. .................................. 560/221; 525/531; 526/240; 526/312; 528/114
[58] Field of Search ...................... 526/240, 241, 312; 525/531; 528/114; 560/220, 221, 222

[56] References Cited

U.S. PATENT DOCUMENTS

| | | |
|---|---|---|
| 2,824,851 | 2/1958 | Hall . |
| 2,925,403 | 2/1960 | Dekal . |
| 2,947,338 | 8/1960 | Reid . |
| 2,967,840 | 1/1961 | Phillips . |
| 3,066,112 | 11/1962 | Bowen . |
| 3,194,783 | 4/1965 | Bowen . |
| 3,287,155 | 11/1966 | Munn . |
| 3,294,865 | 12/1966 | Price . |
| 3,373,221 | 3/1968 | May . |
| 3,507,041 | 4/1970 | Waliaven . |
| 3,539,526 | 11/1970 | Bowen . |
| 3,539,533 | 11/1970 | Lee . |
| 3,628,988 | 12/1971 | Stol . |
| 3,635,889 | 1/1972 | Bowen . |
| 3,719,623 | 1/1973 | Bowen . |
| 3,740,850 | 6/1973 | Bowen . |
| 3,751,399 | 7/1973 | Lee . |
| 3,766,132 | 8/1973 | Lee . |
| 3,774,305 | 11/1973 | Stoffey . |
| 3,785,832 | 1/1974 | Bowen . |
| 3,787,521 | 1/1974 | Lauana . |
| 3,815,239 | 6/1974 | Lee . |
| 3,825,518 | 7/1974 | Foster . |
| 3,930,076 | 12/1975 | Kliment . |
| 3,991,133 | 11/1976 | Siwiec . |
| 4,072,592 | 2/1978 | Due . |
| 4,097,994 | 7/1978 | Reaville . |
| 4,130,702 | 12/1978 | Choe .................................. 526/240 |

OTHER PUBLICATIONS

Silverstone and Dogon (Eds.), *The Acid Etch Technique*, (1975) [p. 2].
Bowen, "Adhesive Bonding of Various Materials to Hard Tooth Tissues: I. Method of Determining Bond Strength," 44 *J. Dent. Res.*, 690–695 (1965), [pp. 2, 21].
Bowen, "Adhesive Bonding of Various Materials to Hard Tooth Tissues: II. Bonding to Dentin Promoted by Surface-Active Comonomer," 44 *J. Dent. Res.*, 895–902 (1965) [p. 2].
Bowen, "Adhesive Bonding of Various Materials to Hard Tooth Tissues: IX. The Concept of Polyfunctional Surface-Active Comonomers," 9 *J. Biomed. Mater. Res.*, 501–510 (1975) [p. 3].
74 *Chemical Abstracts*, 88756n (1972) [p. 3].
Bowen, "Adhesive Bonding of Various Materials to Hard Tooth Tissues: VII. Metal Salts as Mordants for Coupling Agents," in Moskowitz, H. D., Ward, G. T., and Woolridge, E. D. (Eds.) *Dent. Ad. Mat.*, Proceedings from Symposium Nov. 8–9, 1973, at the Hunter-Bellevue School of Nursing 205–221 (1974) [p. 4].

*Primary Examiner*—Paul R. Michl
*Attorney, Agent, or Firm*—Allegretti, Newitt, Witcoff & McAndrews

[57] ABSTRACT

A family of polyfunctional surface-active comonomers which act to improve the adhesion between a resin or composite material and solid surfaces capable of binding polyvalent cations is described. These polyfunctional surface-active comonomers, or "PolySACs", are preferably the reaction product of an epoxy acrylate or methacrylate and an aminobenzoate. The adhesion of the resin or composite material to certain solid surfaces is also improved by the preparatory treatment of these surfaces with a monobasic acid of intermediate strength followed by treatment with a mordant.

In its most preferred form the invention is employed in reconstructive dental work to improve the adhesion between a resin or composite material and dentin. The dentin is cleansed with isotonic formic acid, treated with an isotonic ferric chloride mordant and then treated with a PolySAC which is the reaction product of an oligomeric diglycidyl ether, acrylic acid and lithium ortho-aminobenzoate. The resin or composite material is then applied.

17 Claims, No Drawings

USE OF A POLYFUNCTIONAL SURFACE-ACTIVE COMONOMER AND OTHER AGENTS TO IMPROVE ADHESION BETWEEN A RESIN OR COMPOSITE MATERIAL AND A SUBSTRATE

BACKGROUND OF THE INVENTION

The invention described herein was made in the course of work under a grant or award from the Department of Health, Education and Welfare.

This is a division of application Ser. No. 10,803, filed Feb. 9, 1979 now U.S. Pat. No. 4,251,565.

This invention relates to the field of improving adhesion between a resin or composite material and a solid surface capable of binding polyvalent cations. Such surfaces include metals or alloys with oxide surfaces; glasses; microcrystalline glasses; ceramics; natural and synthetic minerals; concrete; calcified tissues; hard tissues, especially hard tooth tissues; enamel; and most preferably, dentin.

In reconstructive dentistry, composite resins are applied to the surface of remaining dentin. The need for improved adhesion of dental resin to the dentin by way of a chemical mechanism is broadly recognized, and means to obtain durable adhesive bonding to composite resins to dentin would have immediate utility in dental practice. The technique of etching enamel with acid has resulted in major advances in clinical dentistry; however, the techniques for bonding composite resins to dentin and certain enamel surfaces remain unsatisfactory. See Silverstone and Dogon (eds.), *The Acid Etch Technique* (1975).

Surface-active comonomers that are difunctional (having one chelating group and one polymerizable group per molecule) have been synthesized and tested. See Bowen, "Adhesive Bonding of Various Materials to Hard Tooth Tissues: I. Method of Determining Bond Strength," 44 *J. Dent. Res.* 690–95 (1965); Bowen, "Adhesive Bonding of Various Materials to Hard Tooth Tissues: II. Bonding to Dentin Promoted by Surface-Active Comonomer," 44 *J. Dent. Res.* 895–902 (1965). See also U.S. Pat. No. 3,635,889. These difunctional agents are to be distinguished from the polyfunctional surface-active comonomers, or "PolySACs", of the present invention, which have two or more independent sets of chelating ligand groups and at least one, but preferably two or more, vinyl, vinylidene or other groups capable of homoplymerization and copolymerization with the resin to be bonded to the dentin surface. The need for some type of polyfunctional surface-active comonomer has been recognized on the theoretical level, see Bowen, "Adhesive Bonding Of Various Materials To Hard Tooth Tissues: IX. The Concept of Polyfunctional Surface-Active Comonomers," 9 *J. Biomed. Mater. Res.* 501–10 (1975), but heretofore no specific structures for PolySACs have been proposed and no method for synthesizing PolySACs has been taught in the literature. The present invention makes such compounds available to the art for the first time.

The reactants employed in the synthesis of PolySACs are well known. The acrylates and methacrylates and epoxy acrylates and methacrylates which form the preferred precursors for PolySACs have been known and used in a number of technical fields, including the dental field. See, for example, U.S. Pat. Nos. 3,930,076; 3,628,988; 3,287,155; 3,194,783; 3,740,850; 3,539,526; 3,751,399; 4,072,592; 2,824,851; 3,719,623; 3,066,112; 3,825,518; 3,539,533 and 3,815,239. In some instances, the polymerization of these materials has been catalyzed by amine accelerators. See, for example, U.S. Pat. No. 3,740,850 to Bowen and Argentar. Carboxylic acids and their derivatives have been employed in various roles in connection with acrylates and epoxides. See U.S. Pat. Nos. 3,991,133; 3,294,865; 3,373,221; 2,947,338; 2,967,840 and 3,787,521 and 74 *Chemical Abstracts* 88756n (1971).

Reconstructive dental work is impeded not only by lack of an effective resin-dentin adhesive, but also by the presence of a smeared surface layer on dentin that has been mechanically cut and of a salivary pellicle on the surface of dentin exposed by gingival recession. While strong, polybasic acids such as phosphoric acid or citric acid of various concentrations (usually on the order of 50%) have been proposed as cleansers to be applied to enamel surfaces for periods of a minute or longer, these acids have no beneficial effect in promoting adhesion to dentin and are irritating to the dental pulp tissues. Furthermore, the removal of smeared layers or surface debris by dissolution with polybasic organic acids may result in a dentinal surface with cationic sites blocked by residual molecules or derivatives of these acids. See Bowen, "Adhesive Bonding of Various Materials to Hard Tooth Tissues: VII. Metal Salts as Mordants for Coupling Agents," in Moskowitz, H. D., Ward, G. T., and Woolridge, E. D. (eds.), *Dental Adhesive Materials*, Proceedings from Symposium Nov. 8–9, 1973 at the Hunter-Bellevue School of Nursing 205–21 (1974).

Adhesive techniques which solve these problems in the dental field may be drawn upon to beneficiate adhesion of resins or composite materials to solid surfaces capable of binding polyvalent cations in other contexts.

SUMMARY OF THE INVENTION

It is an object of this invention to provide polyfunctional surface-active comonomers which are the reaction products of an epoxy acrylate or methacrylate and an aminobenzoate.

An additional object of this invention is the use of these PolySACs as adhesives between a resin or composite material and a solid surface capable of binding polyvalent cations.

It is a further object of this invention to employ these PolySACs as dental adhesives between a resin or composite material and dentin.

It is also an object of this invention to provide a nonirritating cleanser which will effectively remove the smeared surface layers or salivary pellicle from dentin or enamel prior to reconstructive dental work. More specifically, it is an object of this invention to employ a monobasic acid of intermediate $pK_a$ (relatively weak) and preferably isotonic concentration (relatively low concentration) to effectively remove the smeared layer or a contaminating layer.

Another object of this invention is the use of a mordant, preferably ferric chloride, to enrich a solid surface capable of binding polyvalent cations, and especially hard tooth tissues, in inorganic cations.

An important object of this invention is the provision of an integrated system for improving the adhesion of a resin or composite material to dentin in reconstructive dentistry which includes effective, nonirritating cleansing of the dentin surface, application of a mordant, and application of a PolySAC adhesive between the dentin and the resin or composite material.

The PolySACs which form one aspect of the present invention are the reaction products of an epoxy acrylate or methacrylate and an aminobenzoate. Preferably, the PolySAC is the reaction product of lithium ortho-aminobenzoate with the reaction product of an oligomeric diglycidyl ether and acrylic acid. Application of such a PolySAC as an interlayer between a resin or composite material and a solid surface capable of binding polyvalent cations, most preferably dentin, increases the strength of the adhesive bond between these two.

The durability of the adhesive bond between dentin and a composite resin is also increased by cleansing of the dentin surface with an isotonic acid of intermediate strength. In a preferred embodiment of the invention, the cleanser employed is isotonic formic acid. The dentin surface is then enriched in inorganic cations by the application of a mordant, preferably an aqueous, isotonic ferric chloride solution. The isotonicity of the acid or mordant solution will reduce detrimental effects, if any, on the health of the dental pulp tissues.

DESCRIPTION OF THE PREFERRED EMBODIMENTS

The inventive PolySACs may be prepared by the additiopresence of catalysts and free radical polymerization inhibitors, followed by the reaction of this intermediate with a stoichiometric quantity of an aminobenzoate.

Acrylic acid and methacrylic acid each offer distinct advantages as precursors in the synthesis of the PolySACs. The advantages which may accrue from use of acrylic acid stem from steric considerations. The backbone chains of polymethacrylates are relatively straight and stiff due to crowding of the methyl and carboxylate substituents. In contrast, polyacrylates have flexible chains. The terminal acrylate or methacrylate groups in the PolySAC provide the site for bonding of the PolySAC interlayer to the composite resin (usually a methacrylate) via polymerization. Acrylates and methacrylates can copolymerize, and it is expected that an acrylate-methacrylate mixture, at or very near a solid (the dentin substrate or other solid surface capable of binding polyvalent cations) would have more degrees of freedom and would probably polymerize more completely than a methacrylate-methacrylate combination.

In constrast, methacrylic acid as a PolySAC precursor offers as potential advantages a harder adhesive interlayer, greater color stability, and greater stability against premature polymerization.

While acrylic acid and methacrylic acid are preferred precursors for PolySAC synthesis at least when the PolySAC is to be employed in the dental field, other monomers of types well known in the art which are capable of free radical polymerization may be substituted for these.

The preferred epoxy precursors for use in this invention are the commercially available diglycidyl ethers of a bisphenol A oligomer. These epoxy precursors offer the advantage of chemical similarity to the methacrylate-based common dental resins, such as BIS-GMA (described in U.S. Pat. Nos. 3,066,112; 3,179,623; 3,194,783 and 3,194,784) with consequent miscibility between PolySAC and resin. The most preferred epoxy precursor is of the formula:

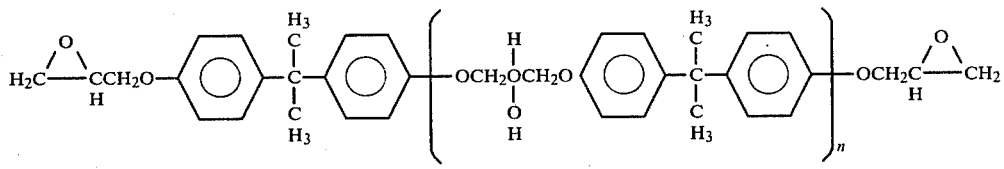

where n varies between 0 and 2, but averages 0 to 1. Other diepoxides, and also polyepoxides of higher functionality, may be employed under certain conditions, but may exhibit reduced miscibility with BIS-GMA resins. Examples of alternative diepoxides and polyepoxides include the diglycidyl ether of resorcinol, o-glycidyl phenyl glycidyl ether, polyglycidyl ether of o-cresol-formaldehyde novolac, polyglycidyl ether of phenol-formaldehyde novolac and di(2-methyl) glycidyl ether of ethylene glycol. Epoxides of functionalities greater than two may be used provided that, as with diepoxides, the proportions of the reactants are such that a polyepoxide with q epoxide groups per molecule reacts with q-1 molecules of acrylic or methacrylic acid. For a dipoxide, for example, one mole of acrylic or methacrylic acid is reacted with one mole of diepoxide (two epoxy groups).

The reaction products of the first reaction step, for acrylic acid and the preferred epoxide as the reagents, include:

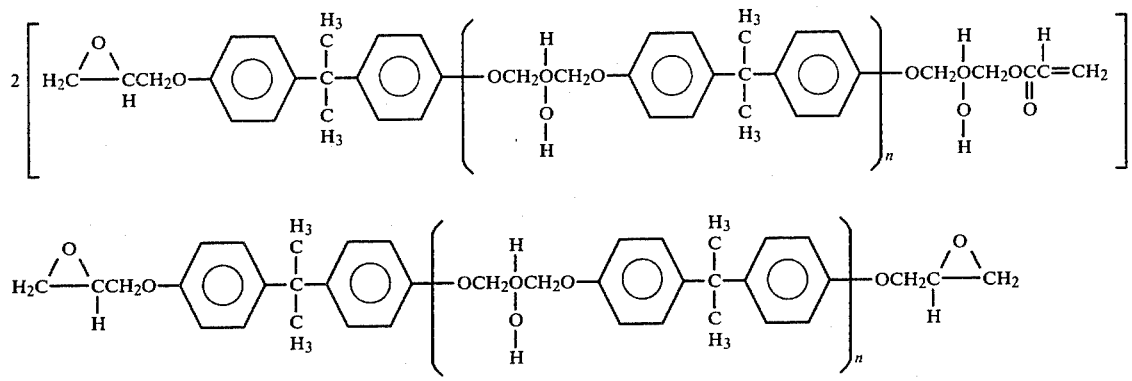

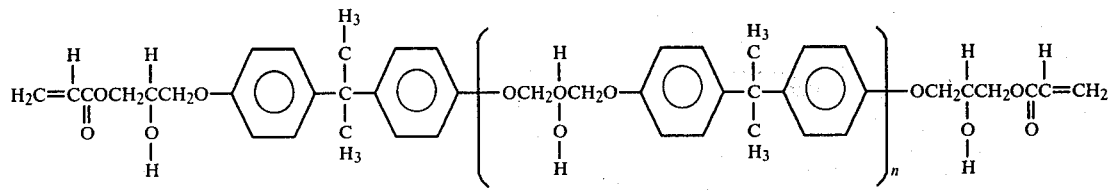

It is believed that the diacrylates or dimethacrylates formed neither significantly contribute to nor detract from the effectiveness of the PolySAC, and the entire reaction product mixture may be used as an adhesive.

The epoxide-acid addition reaction is carried out in the presence of a catalyst and a free radical polymerization inhibitor. Preferred compounds which perform these functions include triphenylantimony (triphenylstibene) or triphenylphosphine, both disclosed in U.S. Pat. No. 3,317,465. Alternative catalysts include triethylamine and other tertiary amines; alternative inhibitors include methyl hydroquinone, monomethyl ether of hydroquinone and butylated hydroxytoluene (BHT). Other catalysts and inhibitors well known in the art may be substituted.

The aminobenzoate reactant is ordinarily a univalent alkali metal salt, preferably a lithium salt, of an aminobenzoic acid. Sodium, potassium, or other bases such as tertiary amines which would form this type of salt may be used instead of lithium. While ortho-, meta- or para-aminobenzoate may be employed, ortho-aminobenzoate is much preferred because it permits the nitrogen of the amino group and the acidic oxygen of the carboxylic acid group to approximate the same cation on the dentin or other substrate surface.

The structure of a preferred class of PolySACs, those PolySACs in which the epoxy precursor is a diglycidyl ether of a bisphenol A oligomer, is

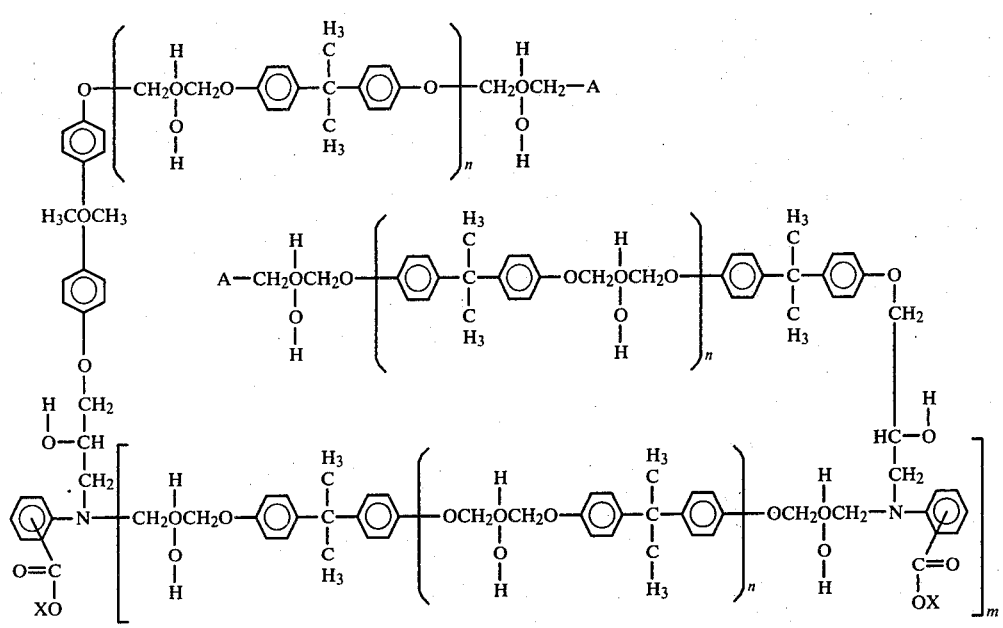

I where A is a monomer polymerizable by free radical polymerization, X is a univalent alkali metal cation, m is an integer which may vary between 0 and 10, n is an integer which may vary between 0 and 2, and the aminobenzoate structure

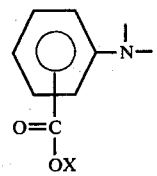

represents ortho-, meta- or para-aminobenxoate.

The most preferred PolySAC of the present invention is of the formula

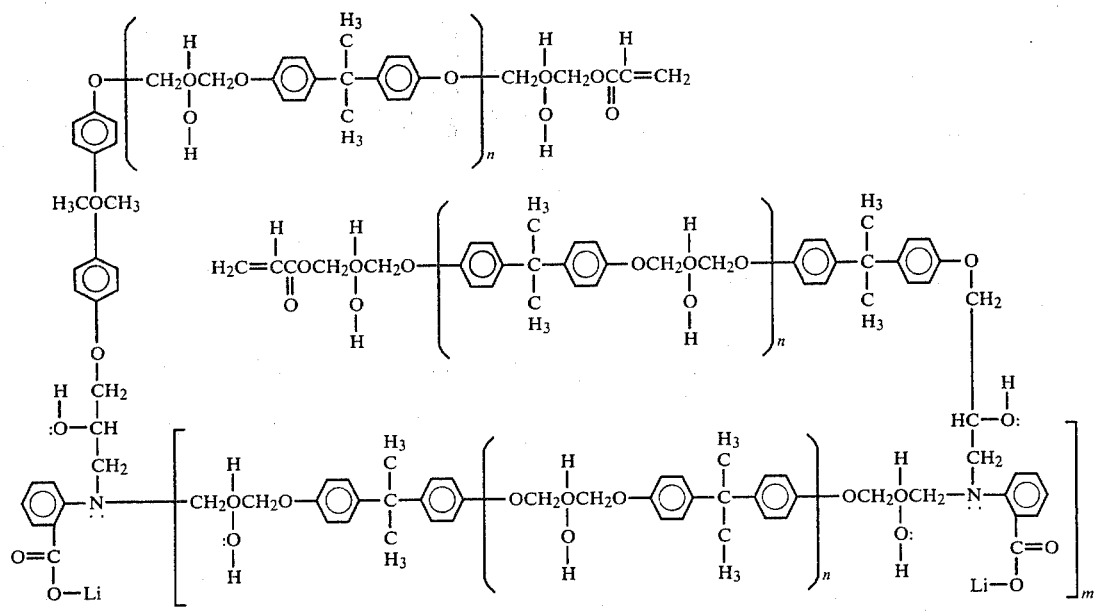

where m is an integer which may vary between 0 and 10 and n is an integer which may vary between 0 and 2. The symbol : indicates an electron pair which is available to coordinate with a cation on the solid substrate. In the most preferred class, four ligands could approximate a single such cation.

The synthesis of any given PolySAC is likely to result in a product mixture including PolySACs of varying n and m, and other by-products. The value of n will ordinarily vary because the epoxy precursors are commercially available as mixtures of oligomers with varying n. The value of m will vary in a statistical distribution as a result of the synthesis. Expected by-products include diacrylates or dimethacrylates having no aminobenzoate component.

A PolySAC, dissolved in an appropriate solvent, may be applied directly to any solid capable of binding or taking up on its surface polyvalent cations. Such surfaces include metals or alloys with oxide surfaces, glasses, microcrystalline glasses, ceramics, natural and synthetic minerals, concrete, hard tissues and calcified tissues. In the dental field, the preferred field of application of this invention, such surfaces include hard tooth tissues, particularly enamel, and most preferably, dentin. The application of the PolySAC will improve adhesion of a resin or composite material to the solid surface. In the dental area, reconstructive composite resins which may have their adhesion enhanced by the PolySAC include the commercially available "Adaptic," of Johnson and Johnson, "Blendant," of Kerr Manufacturing Co., "Concise," of 3M Co., and "Vitol," of C. D. Caulk Co. The PolySAC will also improve adhesion of sealant resins, glazes and other dental resins.

The term "resin" as used herein refers to a monomer polymerizable by free radical polymerization. The term "composite material" refers to a mixture of a resin and a filler, ordinarily an inorganic filler.

An additional increase in the strength of a dentin-resin bond may be obtained by cleansing the dentin surface with a monobasic, aqueous, preferably isotonic acid of intermediate strength, or by application of a mordant, or by both these steps in sequence or in combination. The cleanser and mordant may also be employed to increase the strength of the dentin-resin bond independent of the use of a PolySAC.

It has been discovered that acids of intermediate strength ($pK_a$) are superior to both very strong and very weak acids for this application, and an acid concentration that is isotonic with tissue fluids ensures that irritation of the soft tissues will be minimal. Preferably, the $pK_a$ of the acid will lie between 2.5 and 3.8, and the concentration will be isotonic at 0.16 to 0.31 M (depending on the extent of dissociation of the acid). Higher concentrations would be effective, but are not preferred, since they may be expected to lead to irritation of the soft tissues (within the dental pulp) by way of the tubules which connect the dentin surface with the pulp chamber. Monobasic acids are preferred because they are more easily displaced from cationic sites on the solid surface. Representative acids include formic, L-ascorbic and 2-butynoic, and potentially 4-acetyl benzoic, 3-chloropyridinium(HCl), tetrolic, cyanoacetic, 2-chloro-4-nitrobenzoic, propynoic, 2,5-dinitrobenzoic, 2,6-dichlorobenzoic, and dichloroacetic, or a combination of these, it being understood that specific chemical toxicity, solubility, temperature of application, and other considerations must be decisive in the selection of a particular acid or combination of acids for cleansing a given type of substrate. The preferred acid for use in this invention is formic acid.

The use of a mordant may be expected to improve bonding sites on a solid surface capable of binding polyvalent cations. (The term "mordant" is borrowed from the textile industry, in which context is refers to metal ions which are precipitated in or on textile fibers in order to bind mordant dyes, analogous to the PolySACs of the present invention.) In its preferred application, the mordant may be used to improve bonding sites on sound dentin, or to provide sites on a somewhat decalcified surface. Mordant cations which may be employed include iron (III), zinc, copper (II), aluminum and cobalt (II), and potentially chromium (III). Ferric ion is the preferred cation and ferric chloride the preferred mordant, since ferric ion seems to have the greatest affinity with hard tooth tissues. There is reason to expect that polyvalent ions such as these can be bound by organic proteinaceous material, especially under conditions of rising pH.

The PolySAC, acid cleanser, and mordant of this invention could easily be packaged as components of an article of manufacture or "kit", in such a form that a solution of the PolySAC, an aqueous solution of the acid and an aqueous solution of the mordant could be readily prepared.

Representative aspects of the instant invention are illustrated by the followng examples.

EXAMPLE 1

Synthesis of the PolySAC of Formula II

The synthesis is performed in two steps: In the first, an epoxy acrylate is prepared; in the second, the residual epoxy groups of the epoxy acrylate are reacted with the amino groups of-aminobenzoic acid, so as to form chelating moieties on a polymerizable acrylate monomer.

The first step, the preparation of an epoxy acrylate, yields a product that is analogous to the GMA (glycidyl methacrylate) used previously to synthesize NPG-GMA. In the present case, however, the connecting group between the epoxy ring and the polymerizable carbon double bond is much longer and probably has a solubility parameter (cohesive energy density) much more similar to that of the BIS-GMA resin monomer with which it is to be used. The polymerizable group in this instance is an acrylate, rather than methacrylate.

Synthesis of the Epoxy Acrylate

Fundamentally, the reaction involves the addition of acrylic acid to about one half of the epoxy groups of an oligomeric diepoxide. The diepoxide, Epon Resin 836 of Shell Chem. Co., Houston, Tex., has an epoxide equivalent weight (EEW: grams of resin containing one gram equivalent of epoxide groups) of 294 and a "melting point" of 40–50 C. Two EEW of the diepoxide (588 g) are combined with one mole (72 g) of acrylic acid, 0.03% methyl hydroquinone (p-toluhydroquinone; 2,5-dihydroxytoluene), 0.25% of triphenylantimony (triphenylstibene), and 0.75% of triphenylphosphine.

The mixture is stirred at about 100 C. in the air-containing atmosphere for about 4 hours until the acid value reaches 0.2 and the EEW is 690. The product is cooled to about 75 C., run through a paint filter into a metal can, and stored in the dark at room temperature until used in the second synthesis step. The epoxy acrylate product is a clear, yellow solid; it is soluble in methylene chloride (dichloromethane) or acetone, somewhat soluble in methanol or diethyl ether, and practically insoluble in water or heptane. An acetone solution of it hardens within 2 minutes when combined with an acetone solution of benzoyl peroxide and an acetone solution of N,N-bis (2-hydroxyethyl)-p-toluidine.

Synthesis of the PolySac

Basically, this reaction involves the addition of the epoxy acrylate (by way of its residual epoxy groups) to the amino group of lithium o-aminobenzoate.

Ortho-aminobenzoic acid (anthranilic acid; 1.67 g) is combined with a stoichiometric quantity (0.449 g) of lithium carbonate in 8.36 g distilled water. After the foaming subsides, the mixture is warmed, giving a clear yellow solution. To 10.1 g of this solution, containing 1.74 g (0.01216 mol) of lithium o-aminobenzoate, is added 77.3 g of a clear, yellow methylene chloride solution containing 16.8 g [=(0.01216 mol)×(2)×(690 EEW)] of the epoxy acrylate and 0.0841 g of BHT (food grade butylated hydroxytoluene; 2,6-di-tert-butyl-4-methylphenol). To this mixture of two liquid phases is also added 0.0626 g of triphenylantimony and 0.0615 g of triphenylphosphine. After repeated agitation, the mixture is allowed to stand, stoppered, in a tall, narrow beaker for four days at about 25 C. It is then covered loosely with a glass stopper and heated in a steam bath (70±10 C.) for 24 hours with occasional agitation; during this time, while the solvents are evaporated off and the reaction progresses, the reaction mixture changes from a coarse emulsion to a latex, and then to a translucent semi-solid. It is then heated for 3.5 hours at 95-100 C.; the stopper is removed and the container inverted. While still hot, the product is stretched out (in the container) to facilitate removal after it cools to a glassy solid.

EXAMPLE 2

Characterization of the PolySAC

When the epoxy groups of the reactant mixture react with the difunctional primary amino groups of the lithium o-aminobenzoate, the first-formed reaction products are secondary amines. These in turn react again with remaining epoxide groups, at about half the reaction rate, to form tertiary aromatic amines.

The clear, yellow product is an amorphous solid with a faint aromatic odor and no perceptible taste. The product is calculated to be: C, 71.1; H, 6.7; N, 0.91; found: C, 66.9; H, 6.7; and N, 0.96. In the elemental analysis, there is satisfactory agreement for H and N; the slightly low carbon content (relative to the theoretical) would be rationalized if there were some residual water and methylene chloride solvents in the product, which is likely. Based on probability analysis, it is estimated that m in formula II averages 1.0.

Preliminary solubility characteristics are determined with a microscope on very small fragments under cover glasses. It is soluble (miscible) in dimethyl sulfoxide, 2-hydroxyethyl methacrylate (ethylene glycol monomethacrylate), or in a mixture of methanol, acetone, and methylene chloride (10 ml of each). It forms more than one liquid phase, indicating incomplete miscibility, with hydroxypropyl methacrylate, methanol, acetone, methylene chloride, methyl methacrylate, or triethylene glycol dimethacrylate. It is apparently insoluble in water, pentane, or trimethylolpropane trimethyacrylate.

Precipitation by a divalent cation: to a clear solution (from a supernatant aliquot from 0.234 g of the product in 7.896 g of methanol) is added 2 drops of a calcium chloride solution (from 4.2 g $CaCl_2$ in 27.6 g methanol); a immediate turbidity and a voluminous white precipitate result.

Reaction with peroxide: to a clear methanol solution of the product is added a few drops of a clear methanol solution of benzoyl peroxide; the vial is "blown" briefly with nitrogen gas, then capped. Turbidity develops within an hour, is pronounced by 3 hours, and is accompanied by white sediment overnight.

EXAMPLE 3

A cleanser, a mordant, and the PolySAC synthesized in EXAMPLE 1 are evaluated individually and jointly, with controls, to determine their effectiveness in increasing the strength of a dentin-resin bond.

Materials

The cleanser is 0.16 M formic acid buffered by the addition of potassium hydroxide to a pH (theoretical) of 3.15. This concentration is slightly less than isotonic with tissue fluids. Its control is distilled water.

The mordant is isotonic ferric chloride (1.41% $FeCl_3$). Its control is also distilled water.

Sufficient of the PolySAC coupling agent is dissolved in HEMA (2-hydroxyethyl methacrylate; ethylene glycol monomethacrylate) to make a 5.00% solution. The PolySAC is in the lithium salt form and is not fractionated or otherwise purified. Its control is the HEMA without the PolySAC dissolved in it.

The composite resin is a commercial proprietary material, "Adaptic," of Johnson & Johnson, stored under refrigeration between usages.

The dentin substrates are from four third molar teeth taken from a seventeen-year-old male, and stored in distilled water under refrigeration with no chemical preservatives.

Methods

The enamel is removed by wet grinding; the teeth are mounted, and the dentin is surfaced. After resurfacing the dentin on an abrasive cloth strip, one drop of the acidic cleanser solution is placed on the surface and allowed to remain for 30 seconds, after which most of the solution is removed by aspiration from the edges so as to not touch the test surface, and then the surface is rinsed under running distilled water for 10 seconds. The bulk water is removed by suction. This treatment is symbolized by a plus sign under column A in Table 1. The negative sign in Table 1 represents the control treatment which is the same except that distilled water is used.

The second step is treatment with the mordant solution; one drop of the ferric chloride solution is placed on the dentin surface, removed by suction at 30 seconds, and rinsed for 10 seconds with distilled water (plus sign under B in Table 1). The control (minus sign under B in Table 1) is distilled water instead of the ferric chloride solution. After the water is removed by aspiration, the dentin surface is blown "dry" with a filtered, compressed-air stream for 10 seconds.

One drop of the PolySAC coupling agent solution (plus sign under C in Table 1), or its control (minus sign), is placed on the dentin surface for 30 seconds. Most of it is removed by aspiration (suction) as before and then the compressed air stream is directed normal to the center of the surface so as to blow away practically all visible traces of the solution.

Next, the composite material is mixed according to the manufacturer's instructions except that an agate spatula is used to mix the two pastes together. The composite is applied with an apparatus as shown in FIGS. 1 and 2 of Bowen, "Adhesive Bonding of Various Materials to Hard Tooth Tissues: I. Method of Determining Bond Strength," 44 *J. Dent. Res.* 690–95 (1965). This disclosure is expressly incorporated herein and made a part hereof by reference. The mixed material is placed on a stainless steel plunger, the cylindrical stainless steel tube is placed over the part containing the dentin surface and then the iris is placed flat against the dentin surface. The plunger part, containing the mixed composite, is then let down against the dentin surface and compressed there for five seconds under a load giving 1,030 kPa pressure. The load is removed and the assembly is allowed to stand for fifteen minutes before it is immersed in distilled water at room temperature (about 24 C.). After storage for twenty-four±four hours, the tensile force required to break the adhesive but joint, 6 mm in diameter, is measured.

The adhesion data are arranged in standard order, and Yates' algorithm, see HUNTER, J. S., *Design of Experiments Course*, A Westinghouse Learning Press publication 57ff. (1968), is used to calculate the estimated main effects of the three factors and the interactions among them.

TABLE 1

Adhesion Test Results from a $2^3$ Factorial Design
Category: A, cleanser; B, mordant; C, coupling agent.

| A | B | C | Adhesion (kPa) | Estimated effect | (kPa) |
|---|---|---|---|---|---|
| − | − | − | 680 | | |
| + | − | − | 620 | B per se | = 1,060 |
| − | + | − | 1,630 | AB interaction | = 460 |
| + | + | − | 1,730 | ABC interaction | = 380 |
| − | − | + | 1,030 | A per se | = 230 |
| + | − | + | 640 | AC interaction | = 220 |
| − | + | + | 1,280 | C per se | = 210 |
| + | + | + | 2,580 | BC interaction | = 34 |

Results

The outstanding main effect, which is statistically significant, is the benficial effect of the ferric chloride mordant treatment. This treatment forms a barely-visible white reaction product on the dentin surface which, as yet, has not been identified. It contains Fe, as evidenced by nondispersive X-ray analysis. The lowest average adhesion value in which the mordant is used ranks higher than the highest average value wherein it is not used.

The main effects of the cleanser and of the coupling agent are also beneficial, but due to the high variance of the data, the null hypothesis cannot be dismissed as improbable. The cleanser-mordant interaction and the cleanser-coupling agent interaction are also favorable. The two-factor interaction of mordant and coupling agent is trivial but is not negative. The three-factor interaction among cleanser, mordant, and PolySAC coupling agent was also strongly positive, but somewhat below the 95% condifence limit.

Discussion

The fact that all main effects and interactions are positive augurs well for an interpretation that these three treatments are synergistic in improving adhesion between a composite resin and dentin. If a factor or an interaction had a negative value, this would suggest antagonsim, that is, a tendency to lower adhesive values.

Part of the favorable effect of the ferric chloride mordant solution might be related to an augmentation of the degree of polymerization. This kind of benefit cannot be ascribed with any certainty, however, because iron ions can initiate polymerization or inhibit polymerization. See U.S. Pat. No. 2,925,408.

EXAMPLE 4

Comparison Of Various Acids As Cleansers

Materials

The acidic solutions studied are those listed in Table II. Dibasic acids are included for purposes of expediency in order to provide a range of pK values for testing purposes, and are not considered part of the invention.

TABLE II

Experimental 0.16 M Potassium Acid Buffer Solutions

| Compound | pK₁ | pH (theor.) | Solution number |
|---|---|---|---|
| H₂O | | 7 | 1 |
| 3-methyl-2-butenoic (B, B-Dimethylacrylic) | 5.12 | 4.52 | 2 |
| Acetic | 4.76 | 4.16 | 3 |
| L-Ascorbic (chelate) | 4.30 | 3.70 | 4 |
| Itaconic (dibasic) | 3.85 | 3.25 | 5 |
| Formic | 3.75 | 3.15 | 6 |
| L-Ascorbic Acid (0.16 M unbuffered ascorbic acid, vitamin C, pH from The Merck Index, 1968) | | 2.5 | 7 |
| 2-Butynoic (tetrolic) | 2.66 | 2.06 | 8 |
| L-Ascorbic Acid (Unbuffered, 4.76% concentration; pH from The Merck Index, 1968) | | 2.0 | 9 |
| Citraconic (dibasic) | 2.29 | 1.69 | 10 |
| Maleic (dibasic) | 1.94 | 1.34 | 11 |
| Trichloroacetic | 0.64 | 0.04 | 12 |

The concentrations used, unless specified otherwise, are approximately isotonic (isosotic) with plasma to minimize untoward effects from osmotic pressure.

The solutions containing ascorbic acid are prepared immediately before they are used, because of their tendency toward oxidation.

An erupted, noncarious, lower third molar is extracted and stored in the dark in distilled water at 5° C. It is then mounted and sectioned across its long axis with a diamond disc (saw) under running water to provide 12 sequential sections. These are each placed in a separate vial containing distilled water. The tooth specimen is grooved so that each section has notches in it indicating the side and orientation. Each section is divided, with the use of a sharp scalpel, into two or more samples.

Methods

An attempt is made, in the experimental design, to make provision for a possible or conceivable trend in the innate composition of the dentin sections as they originate more and more apical within the tooth specimen. If the acidic solutions are simply taken in order (with a trend in the pH) and applied to the sections in order, any trend in the latter would confound the results. Accordingly, the 12 sequential sections, each divided into a "notched" half, N, and an "unnotched" half U, are rearranged. The odd numbered samples in both groups are reversed in order (odd is decided by coin flip). Then, randomly, one of these two new sequences is totally reversed.

Each sample is held with needle-nosed tweezers in a given location (identified by a drawing) and one half of each portion is then covered with poly(tetrafluoroethylene) tape and held under pressure at the edge with a different pair of tweezers. This provides a "control" region on each piece. The surface is rinsed with distilled water, and then blown free of bulk water with a filtered air stream. Then, 3 drops of treatment solution are applied to the surface from a stock solution by way of a disposable glass pipette. The solution is in contact with the surface for 30 seconds (no rubbing), after which the surface is rinsed for 10 seconds under running distilled water. It is blown free of water, the tape is removed, the surface is rinsed a few seconds again with distilled water, and then blown free of visible moisture. The sample is placed on double-stick tape on a stub for SEM (scanning electron microscopy), and covered by an inverted beaker to dry overnight.

The mounted samples are sputter-coated with gold/palladium in preparation for SEM. The process is pulsed to minimize heating and desiccation artifacts. The samples of the stubs are identified with a new series of code numbers so that the acids used for treatment are not known at the time of microscopy or during the first evaluations of pictures.

To add obectivity, the experimental design also includes a plan to judge the relative strengths of the acids by the appearances of the micrographs.

The photomicrographs of these surfaces are arranged according to two criteria. The first consideration is the amount of the smeared layer removed, and the second relates to overall homogeneity. Pictures (surfaces represented) are ranked 1 to 24 with respect to the apparent strength of the acid used.

Results

The subjective ranking gives the ordered arrangement in Table III. The "original ranking" is from pictures of the two sets of 12 samples, N (notched) and U (unnotched), in terms of solution numbers used in their preparations.

After these "blind" relationships are judged by the appearance of the photomicrographs, the code is broken. The pictures, rearranged as necessary, yield the following information from the appearance of the micrographs.

(1) The distilled water leaves both smooth, smeared areas and also regions rough with piled but cohesive debris.

(2) The 3-methyl-2-butenoic acid buffer appears to have no effect greater than that of water.

(3) The acetic acid buffer seems to give a somewhat cleaner surface but there remains a layer of material over the tubule openings and there is "mud-cracked" material in the cutting grooves.

(4) The ascorbic acid buffer seems to have little or no effect. In fact, there remains more loose surface debris and "accretions" than after acetic acid buffer was used.

(5) The itaconic acid buffer appears to remove most debris and open the tubules. Its anomalous activity leads to higher ranking, as if it were a stronger acid than formic or maleic.

(6) The formic acid buffer opens tubules somewhat; tubular contents remains in the tubules, however. There is some debris remaining in the grooved areas.

(7) The unbuffered ascorbic acid (0.16 M) seems to remove most of the debris and to leave a fairly clean surface. The tubular positions or locations are obvious, but they are mostly filled with solid material. This surface has the best appearance.

(8) The 2-butenoic acid buffer opens at least half of the tubules but, nonetheless, leaves fine debris in striations on the surface. There are some globules, suggesting a precipitate. (A mixture of acids might be less inclined to produce crystallized precipitates than would the equivalent amount of a single kind of acid buffer.)

(9) The 4.76% ascorbic acid gives results similar to the 0.16 M ascorbic acid except that there may be somewhat more open space around the tubular contents.

(10) The citraconic acid buffer rounds off the margins at the tubular openings and leaves a somewhat reduced amount of tubular contents appearing at the openings. Nonetheless, it leaves debris in the larger grooves.

(11) The maleic acid buffer opens and empties the tubules in some cases, and leaves a "collar" around the opening. In other areas, large quantities of material are left in the deeper grooves; the material forms mud cracks upon drying in the vacuum.

(12) The trichloroacetic acid buffer gives a strongly etched appearance, with enlarged tubular openings. It is manifestly much too potent for this application.

TABLE III

Ranking of solutions based on their subjective, apparent effects on cut dentin surfaces (replicate samples, N and U); SEM photomicrographs are coded and ranked "blind", according to the degree of change (removal and smear layer).

| Original ranking | First series of samples, N | Second series, U | Average ranking | Solution number | Average mismatch |
|---|---|---|---|---|---|
| 1 N<br>2 N | 1 | 2 | 1.5 | 1 | 0.5 |
| 2 U<br>1 U | 2 | 1 | 1.5 | 2 | −0.5 |
| 4 U<br>3 N | 3 | 4 | 3.5 | 3 | 0.5 |
| 4 N<br>3 U | 4 | 3 | 3.5 | 4 | −0.5 |
| 6 N<br>11 U | 6 | 11 | 9.5 | 5 | 4.5 |
| 7 U<br>9 N | 9 | 7 | 6.0 | 6 | 0.0 |
| 8 N<br>7 N | 8 | 6 | 7.0 | 7 | 0.0 |
| 6 U<br>5 U | 7 | 5 | 9.0 | 8 | 1.0 |
| 9 U<br>10 U | 11 | 9 | 7.5 | 9 | −1.5 |
| 8 U<br>11 N | 10 | 10 | 10.0 | 10 | 0.0 |
| 10 N<br>5 N | 5 | 8 | 7.0 | 11 | −4.0 |
| 12 U | 12 | 12 | 12.0 | 12 | 0.0 |

It should be understood that the foregoing disclosure emphasizes certain specific embodiments of the invention and that all modifications or alternatives equivalent thereto are within the spirit or scope of the invention as set forth in the appended claims.

I claim:

1. A compound, useful as an adhesive between a resin or composite material and a solid surface capable of binding polyvalent cations, of the formula

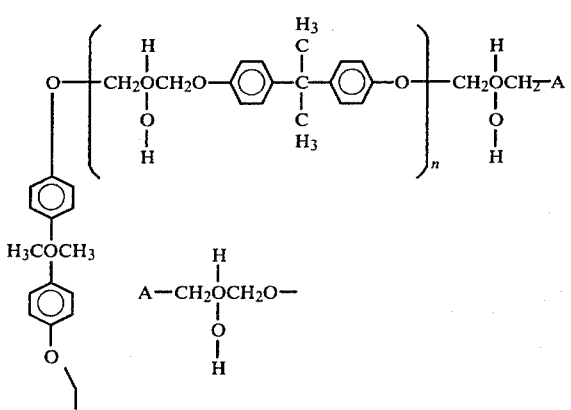

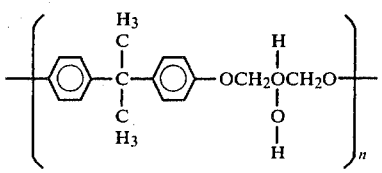

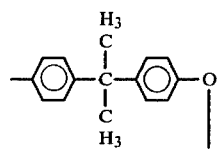

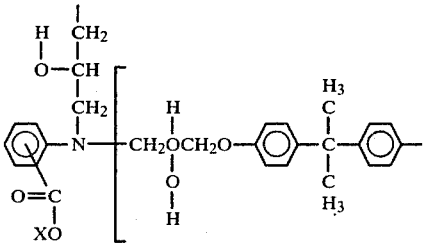

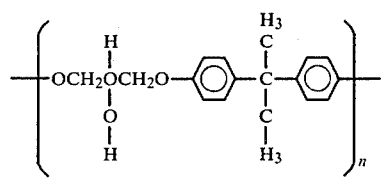

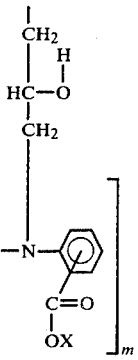

where A is a monomer polymerizable by free radical polymerization, X is a univalent metal cation, m is an integer which may vary between 0 and 10, n is an integer which may vary between 0 and 2, and the aminobenzoate structure

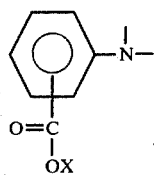

represents ortho-, meta- or para-aminobenzoate.

2. A compound as in claim 1 wherein A is acrylate or methacrylate.

3. A compound as in claim 1 wherein the aminobenzoate is ortho-aminobenzoate.

4. A compound as in claim 1 wherein A is acrylate and the aminobenzoate is ortho-aminobenzoate.

5. A compound as in claim 1 wherein A is acrylate, X is lithium and the aminobenzoate is ortho-aminobenzoate.

6. The reaction product, useful as an adhesive between a resin or composite material and a solid surface capable of binding polyvalent cations, of
  (a) the addition of a monomer polymerizable by free radical polymerization to all but one of the epoxy groups of a polyepoxide to form an intermediate,
  (b) followed by the reaction of this intermediate with an aminobenzoate.

7. The reaction product as in claim 6 wherein the monomer polymerizable by free radical polymerization is acrylate acid or methacrylic acid.

8. The reaction product as in claim 7 wherein the polyepoxide is selected from the group consisting of the diglycidyl ether of a bisphenol A oligomer, the diglycidyl ether of resorcinol, ortho-glycidyl phenyl glycidyl ether, polyglycidyl ether of ortho-cresol-formaldehyde novolac, polyglycidyl ether of phenol formaldehyde novolac and di(2-methyl) glycidyl ether of ethylene glycol.

9. The reaction product as in claim 8 wherein the aminobenzoate is ortho-aminobenzoate.

10. The reaction product as in claim 9 wherein the polyepoxide is the diglycidyl ether of a bisphenol A oligomer.

11. A dental adhesive composition comprising a compound as in claim 1 or 4 dissolved in a solvent.

12. A dental adhesive composition comprising a reaction product as in claim 6 or 10 dissolved in a solvent.

13. An article of manufacture comprising as components thereof:
  (a) a monobasic acid,
  (b) a mordant, and
  (c) a polyfunctional surface-active comonomer comprising a compound as in claim 1 or 4.

14. An article of manufacture comprising as components thereof:
  (a) a monobasic acid,
  (b) a mordant and
  (c) a reaction product as in claim 6 or 10.

15. A compound as in claim 1 wherein A is methacrylate and the aminobenzoate is ortho-aminobenzoate.

16. An article of manufacture comprising as components thereof:
  (a) a monobasic acid of intermediate strength,
  (b) a mordant selected from the group consisting of iron (III), zinc, copper (II), aluminum, cobalt (II) and chromium (III), and
  (c) a polyfunctional surface-active comonomer comprising a compound as in claim 1 or 4.

17. An article of manufacture comprising as components thereof:
  (a) a monobasic acid of intermediate strength,
  (b) a mordant selected from the group consisting of iron (III), zinc, copper (II), aluminum, cobalt (II) and chromium (III), and
  (c) a reaction product as in claim 6 or 10.

* * * * *